United States Patent [19]

Matsuo et al.

[11] Patent Number: 4,904,763
[45] Date of Patent: Feb. 27, 1990

[54] PHYSIOLOGICALLY-ACTIVE NOVEL PEPTIDES

[75] Inventors: Hisayuki Matsuo; Kenji Kangawa; Naoto Minamino, all of Miyazaki; Tetsuji Sudoh, Tokyo; Atsushi Izumi, Tokyo; Mitsutaka Isogai, Ibaraki, all of Japan

[73] Assignees: Daiichi Pure Chemicals Co., Ltd., Tokyo; Hisayuki Matsuo, Miyazaki, both of Japan

[21] Appl. No.: 207,855

[22] Filed: Jun. 17, 1988

[30] Foreign Application Priority Data

Jun. 17, 1987 [JP] Japan .................... 62-150853

[51] Int. Cl.⁴ .................... C07K 7/10; A61K 37/02
[52] U.S. Cl. .................... 530/324; 530/325; 530/326; 514/13; 514/12
[58] Field of Search .................... 514/929, 12, 13; 530/324, 325, 326

[56] References Cited

PUBLICATIONS

"Antidipsogenic Action of a Novel Peptide, 'Brain Natriuretic Peptide' in Rats", Itoh et al., *Eur. J. Pharm.*, 150 (1988), 193–196.

"Brain Natriuretic Factor", Song and Kohse and Murad, *FEBS Letters,* vol. 232 (No. 1), (May 1988), 125–129.

"A New Natriuretic Peptide in Porcine Brain", Sudoh et al., *Nature,* 332, (1988), 78–81.

"Atrial Natriuretic Peptide in the Brain: Implication of Central Cardiovascular Control", Nakao et al., J. of Hypertension, 4 (6), (1986), S492.

Tanaka et al., Biochem. Biophys. Res. Commun., 124 (2), (1984), pp. 663–668.

Lazure et al., Febs, 172 (1), (1984), pp. 80–86.

Forssmann et al., Anat. Embryol, 168, (1983), pp. 307–313.

Forssmann et al., Cell Tissue Res., 238, (1984), 425–430.

Review Article, Flynn et al., Biochem, 232, (1985), pp. 313–321.

Shiono et al., Biochem. Biophys. Res. Commun., 135 (3), (1986), pp. 728–734.

*Primary Examiner*—Howard E. Schain
*Assistant Examiner*—Susan Perkins
*Attorney, Agent, or Firm*—Oblon, Spivak, McClelland, Maier & Neustadt

[57] ABSTRACT

Disclosed herein is a physiologically-active peptide represented by the following general formula (I):

X—Cys—Phe—Gly—Arg—Arg—Leu—Asp—Arg—Ile  (I)

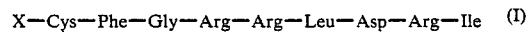

—Gly—Ser—Leu—Ser—Gly—Leu—Gly—Cys—Y
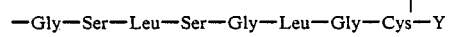

wherein X means H or H-Asp-Ser-Gly- and Y denotes -Asn-Val-Leu-Arg-Arg-Tyr-OH, -Asn-Val-Leu-Arg-Arg-OH, -Asn-Val-Leu-Arg-Tyr-OH, -Asn-Val-Leu-Arg-OH, -Asn-Val-Leu-OH or -Asn-Ser-Phe-Arg-Tyr-OH, or a salt thereof.

10 Claims, 5 Drawing Sheets

PHYSIOLOGICALLY-ACTIVE NOVEL PEPTIDES

BACKGROUND OF THE INVENTION (i) Field of the Invention

This invention relates to physiologically-active novel peptides, more specifically, physiologically-active peptides having smooth muscle relaxing action, diuresis, natriuresis, vasodilation action, antihypertensive action and the like, as well as salts thereof.

(ii) Description of the Related Art

Owing to the advancement in purification and analytical equipment such as high-performance liquid chromatography, amino acid analysis and vapor-phase sequencer, peptides which exhibit interesting physiological activities in a trace amount have been discovered one after another in recent years, thereby making it clearer that a peptide takes an important role as a neurotransmitter or endocrine hormone in living bodies. For example, isolation and identification have been carried out on peptides showing an action similar to conventional amine-based neurotransmitters, such as substance P, neurotensin, vasoactive intestinal polypeptide, neuromesine K and neuromesine L; hormone-like peptides which exist in the hypothalamus and control the secretion of pituitary hormones, such as LH-RH, thyrotrophin releasing hormone (TRH) and growth hormone releasing hormone (GRH); peptides of endogenous nerve factors having opiate activity, such as enkephalin and endorphin; peptides resembling endocrine hormones, such as insulin, calcitonin and atrial natriuretic polypeptide; etc. The investigation of peptides has now been carried on in the molecular level.

In addition, the application of these peptides as therapeutics and diagnostics has also been investigated, resulting in the utilization of some of the peptides as medicines.

SUMMARY OF THE INVENTION

There are however still a number of physiologically-active unknown peptides in living bodies. It is hence extremely important for the development of new therapeutics and diagnostics to isolate such peptides and to investigate their physiological activities.

Under the above-descried circumstances, the present inventors isolated various physiologically-active peptides from the porcine brain by using their smooth muscle relaxing action as an index and investigated their structures and biological activities. As a result, it was found that a novel peptide is included in these peptides. The present inventors synthesized derivatives of the novel peptide, and have proceeded with a further investigation as to pharmacological effects of the novel peptide and derivatives thereof. As a result, it has now been found that these peptides have smooth muscle relaxing action, diuresis, natriuresis, antihypertensive action, etc., leading to completion of this invention.

Namely, this invention provides a physiologically-active peptide represented by the following general formula (I):

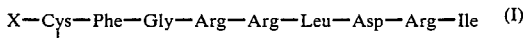
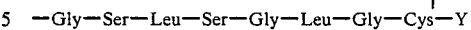

wherein X means H or H-Asp-Ser-Gly- and Y denotes -Asn-Val-Leu-Arg-Arg-Tyr-OH, -Asn-Val-Leu-Arg-Arg-OH, -Asn-Val-Leu-Arg-Tyr-OH, -Asn-Val-Leu-Arg-OH, -Asn-Val-Leu-OH or -Asn-Ser-Phe-Arg-Tyr-OH, or a salt thereof.

The peptides of this invention thus obtained have smooth muscle relaxing action, diuresis and natriuresis, antihypertensive action, etc. Investigation results on these effects are as follows.

(1) Smooth muscle relaxing action:

(1-1) Testing method:

The rectum of each chick (4-6 days old) was enucleated, and then immersed in Kreves-Henseleit nutrient solution which was contained in a 3-ml organ bath. The nutrient solution in the organ bath was fed with a 95% $O_2$–5% $CO_2$ gas and was maintained at 32° C. The muscle sample (length: 1.5 cm) was left over under a static pressure of 0.5 g. When the active exercise of the muscle sample became stable, a test substance was applied and the resulting relaxation of the muscle sample was measured for 8-10 minutes. The organ bath was washed immediately after the measurement, and the above procedure was repeated with intervals of 20-30 minutes. The test substance was used by dissolving a predetermined amount thereof in physiological saline.

(1-2) Results:

Results are shown in FIG. 1(A) through FIG. 1(E). As a result, the peptides of this invention have been found to show strong smooth muscle relaxing action when applied in amounts of 2-5 ng.

(2) Diuresis and natriuresis:

(2-1) Testing method:

Each male SD rat (body weight: 300-400 g) was anesthetized with pentobarbital. His hypogastrium was subjected to incision and a cannula was inserted to the bladder. The amount of urine collected in the above-described manner was measured. A test substance was injected through the femoral vein. In addition, Ringer's solution was injected at a rate of 1.3-1.5 ml/hr through the femoral vein during the experiment.

The collection of urine was conducted for 30 minutes before the administration of the test substance, for 5 minutes after the administration, and periodically thereafter. The diuretic and natriuretic effects of the test substance were determined based on the ratios of the amount of urine and the excreted amounts of Na, K and Cl for the 15-minute period after the administration to their corresponding amounts for the 15-minute period before the administration. The analysis of the electrolytes in each urine sample was performed by "System E4A" (trade name) manufactured by Beckman Industrial Corporation. Each test substance was used after dissolving it together with mannitol, glycin and bacitracin in 50 μl of distilled water so as to achieve isotonicity.

(2-2) Results:

Results are shown in Table 1. As a result, the peptide of this invention has been found to exhibit diuresis even at about 0.1 nmol.

TABLE 1

| Peptide A (nmol) | Amount of urine (%) | Excreted amount of Na, % | Excreted amount of K, % | Excreted amount of Cl, % |
|---|---|---|---|---|
| 0.1 | 121 ± 27 (n = 6) | 133 ± 4 (n = 6) | 120 ± 16 (n = 6) | 154 ± 44 (n = 6) |
| 0.2 | 227 ± 42 (n = 7) | 376 ± 311 (n = 7) | 210 ± 95 (n = 7) | 274 ± 60 (n = 7) |
| 0.4 | 368 ± 110 (n = 5) | 950 ± 291 (n = 5) | 254 ± 85 (n = 5) | 497 ± 161 (n = 5) |

(3) Antihypertensive action:
(3-1) Testing method:
Each male SD rat (body weight: 300-400 g) was anesthetized with pentobarbital. Variations in blood pressure were recorded by calorimeter ("WT-645G", trade name; manufactured by Nihon Kohden Corporation) via a blood pressure transducer ("TP-200T", trade name; manufactured by Nihon Kohden Corporation) through a cannula inserted in the carotid.

A test substance was administered in the same manner as in the diuresis test.

(3-2) Results:
Results are shown in FIG. 2(A) and FIG. 2(B). As a result, it has been found that the peptides of this invention lower the blood pressure by 15-20 mmHg at 0.4 nmol.

As has been described above, the peptides of this invention and their salts have excellent smooth muscle relaxing action, diuresis and natriuresis, and antihypertensive action, and are useful as medicaments, for example, for cardiac edema, nephric edema, hepatic edema, pulmonary edema, hypertension, congestive heart failure, acute and chronic renal failure and the like.

BRIEF DESCRIPTION OF THE DRAWINGS

The above and other objects, features and advantages of the present invention will become apparent from the following description and the appended claim, taken in conjunction with the accompanying drawings, in which:

DETAILED DESCRIPTION OF THE INVENTION AND PREFERRED EMBODIMENTS

Figure 1A:
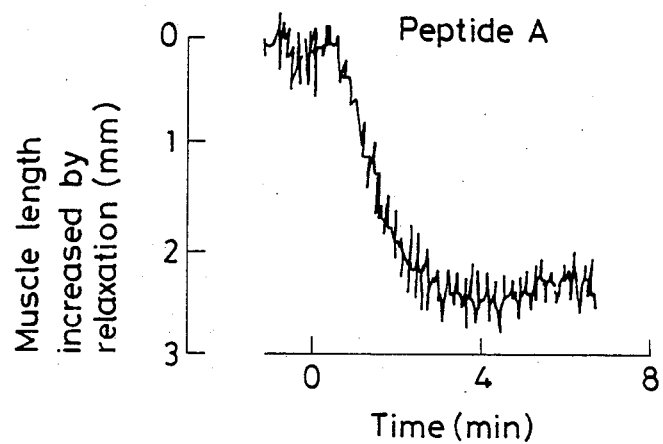
FIG. 1(A) through FIG. 1(E) are diagrammatic representations showing time-dependent variations in muscle length increased by relaxation upon administration of peptides (5 ng) of this invention to chick rectum samples.
Figure 1B:
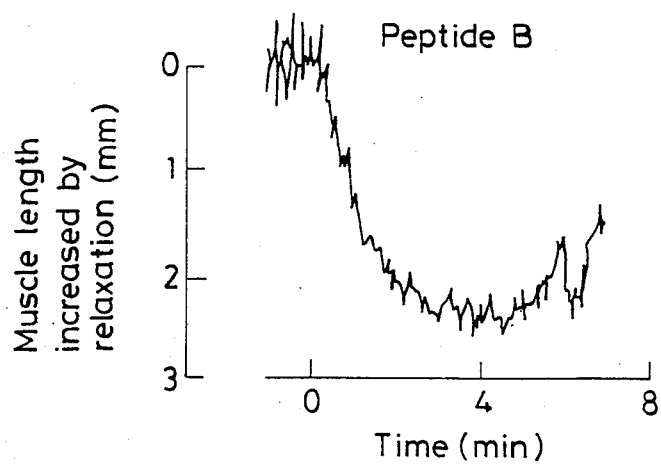
Figure 1C:
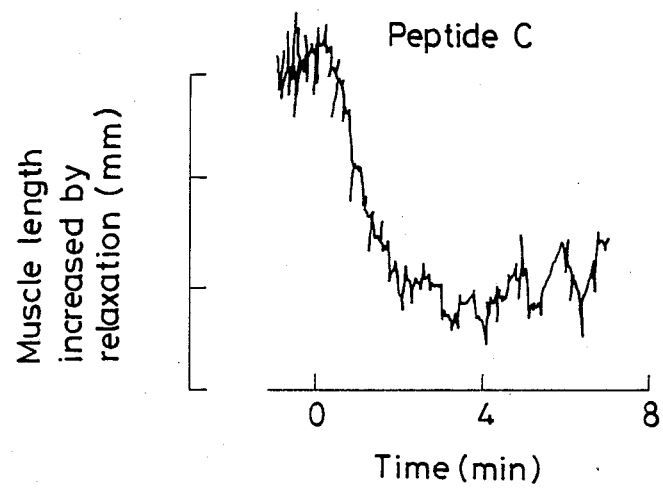
Figure 1D:
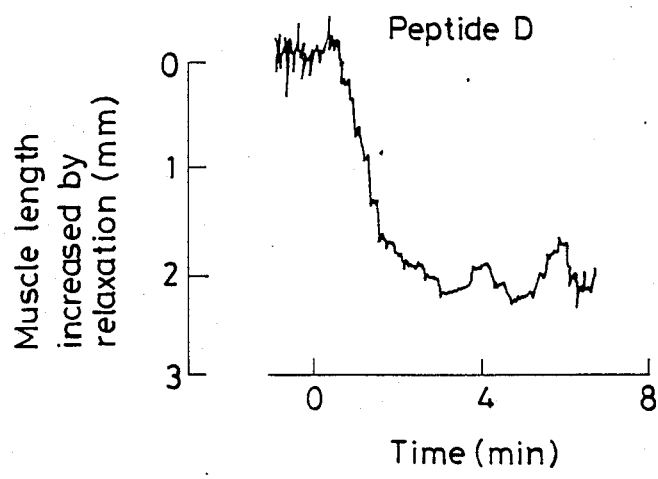
Figure 1E:
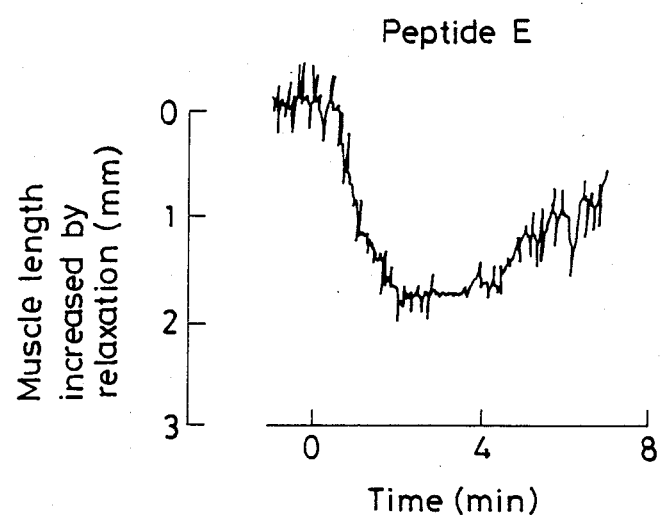
Figure 2A:
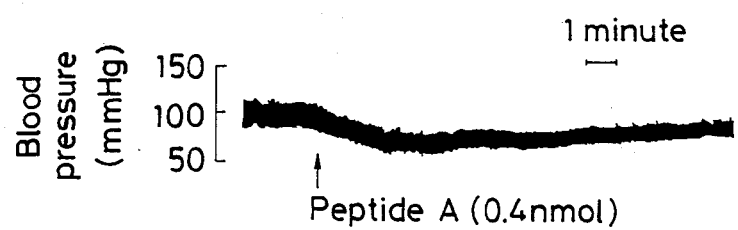
FIG. 2(A) and FIG. 2(B) diagrammatically illustrate variations in blood pressure upon administration of peptides of this invention to rats.
Figure 2B:
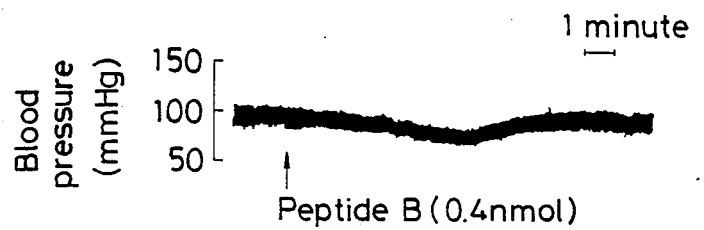

The abbreviations as used herein in the peptide of this invention are generally employed in the present field of art and have the following meanings.

Asp: L-aspartic acid
Ser: L-serine
Gly: glycine
Cys: L-cysteine
Phe: L-phenylalanine
Arg: L-arginine
Leu: L-leucine
Ile: L-isoleucine
Asn: L-asparagine
Val: L-valine
Tyr: L-tyrosine Among the peptides (I) of the present invention, the peptide represented by the following formula:

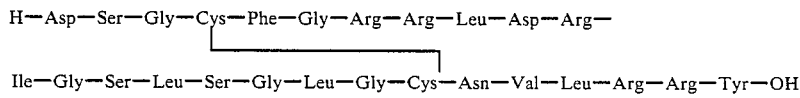

```
H—Asp—Ser—Gly—Cys—Phe—Gly—Arg—Arg—Leu—Asp—Arg—
                   |                                          |
              Ile—Gly—Ser—Leu—Ser—Gly—Leu—Gly—Cys—Asn—Val—Leu—Arg—Arg—Tyr—OH
```

(hereinafter called "Peptide A") can be obtained by its extraction and isolation from procine brains or by its synthesis. The remaining peptides of this invention can be produced synthetically.

The extraction and isolation of Peptide A from porcine brains may be effected, for example, in the following manner. Porcine brains are homogenized in a suitable aqueous acidic solvent. Upon centrifugal separation of any insoluble matter, an extract is obtained. The extract is thereafter processed by methods employed commonly for the purification of peptides and known per se in the art, such as fractional precipitation in an organic solvent, solvent extraction, dialysis, ultrafiltration, gel filtration, ion-exchange chromatography, adsorption chromatography, high-performance liquid chromatography and/or the like, whereby a substance having the corresponding molecular weight is obtained.

The peptides (I) according to this invention can be produced in accordance with the solid phase technique or liquid phase technique employed commonly for the synthesis of peptides [for example, Nobuo Izumiya et al.: "Peptide Gosei (Synthesis of Peptides)", 1984, Maruzen Company Ltd.; The Chemical Society of Japan: "Seikagaku Jikken Koza (I)/Tanpakushitsu no Kagaku (Handbook of Biochemical Experiments (I)/Protein Chemistry)", Vol. 4, pp 208-495, 1977, Kabushiki Kaisha Tokyo Kagaku Dojin].

When the peptides (I) of this invention are synthesized by the solid phase technique by way of example, it is preferable to protect the α-amino group of each amino acid, which is to be used, with a tertbutyloxycarbonyl group (Boc group), the β-carboxyl group of aspartic acid with a benzyloxy group (OBzl group), the guanidino group of arginine with a tosyl group (Tos group), the hydroxyl group of serine with a benzyl group (Bzl group), the hydroxyl group of tyrosine with a 2,6-dichlorobenzyl group (Cl₂-Bzl group), and the thiol group of cystein with an acetoamidomethyl group (Acm group). It is preferable to use a chloromethyl resin or hydroxymethyl resin as an insoluble resin. Condensation of the protected amino acids may preferably be carried out by the dicyclohexylcarbodiimide (DCC) method, the acid anhydride method making use of DCC, the diphenylphosphoric azide (DPPA) method, or the like.

In order to produce each of the peptides (I) of this invention by the solid phase technique, the following procedure may be followed by way of example. First of all, a protected derivative Boc-Tyr(Cl$_2$-Bzl)OH of Tyr which is a C-terminal amino acid is introduced into the chloromethyl resin. The corresponding protected amino acids are then successively caused to couple to synthesize a protected peptide-resin conjugate. The conjugate is thereafter treated with hydrogen fluoride (HF), whereby the cut-off of the peptide from resin and the removal of the protecting groups other than the Acm group are performed simultaneously to obtain a peptide containing the Acm group in place of the thiol group of cystein [Cys(Acm)-peptide]. The resultant peptide is next oxidized with iodine, so that the thiol-protecting group is removed and at the same time, a disulfide bond is formed by the thiol groups of the cystein moieties in the peptide molecule. As a result, a crude synthetic peptide is obtained.

The purification of the thus-obtained crude synthetic peptide can be carried out by a method known per se in the art, for example, by gel filtration ion-exchange chromatography, reversed-phase high-performance liquid chromatography, or the like.

Although those having a shorter carboxyl terminal out of the peptides (I) of this invention may be produced by the above-described production process, they may also be produced by synthesizing their corresponding peptides and then treating the peptides with an enzyme such as carboxypeptidase A or carboxypeptidase B to remove the amino acids of their carboxyl terminals.

By the way, the peptides (I) of this invention may also be converted into acid addition salts with an inorganic acid such as hydrochloric acid, sulfuric acid or phosphoric acid or an organic acid such as formic acid, acetic acid, citric acid, tartaric acid, fumaric acid and maleic acid by a method known per se in the art.

Having generally described the invention, a more complete understanding can be obtained by reference to certain specific examples, which are provided herein for purposes of illustration only and are not intended to be limiting unless otherwise specified.

EXAMPLES

The present invention will next be described in detail by the following Examples.

EXAMPLE 1

Isolation of the natural peptide H—Asp—Ser—Gly—

Cys—Phe—Gly—Arg—Arg—Leu—Asp—Arg—Ile—Gly—Ser—

Leu—Ser—Gly—Leu—Gly—Cys—Asn—Val—Leu—Arg—Arg—Tyr—OH (Peptide A):

About 20 kg of the brains enucleated from 200 pigs immediately after their slaughter were chopped and then added to and boiled in 2 volumes of boiling water, so that the intrinsic protease was deactivated. After cooling the resultant mixture, the mixture was added with acetic acid to a concentration of 1 N and was then homogenized with polytron mixer and extracted at 4° C.

The thus-obtained extract was centrifuged at 12,000×G for 30 minutes, thereby obtaining about 50 l of a supernatant. The supernatant was filtered through a GF/B glass filter (manufactured by Wattman Corporation) to remove suspended fats and was then subjected to ultra filtration ("Pericon Cassette PCAC 1000", trade name; manufactured by Millipore Corporation), whereby the supernatant was desalted and concentrated to a final volume of about 2 l. Acetone was then added dropwise at 4° C. to the thus-prepared solution until the final concentration of acetone reached 75%, so that acetone precipitation was effected. The resultant mixture was centrifuged to obtain about 8 l of a supernatant.

The thus-obtained supernatant was concentrated to dryness under reduced pressure. The residue was dissolved in 0.5 N acetic acid, followed by lyophilization. The lyophilized powder was dissolved in 800 ml of 1 N acetic acid. The resultant solution was processed by chromatography on 400 ml of "sp-Sephadex C-25" (trade name; product of Pharmacia AB), thereby obtaining an acidic fraction (sp-I) eluted with 1N acetic acid, a neutral-mild basic fraction (sp-II) eluted with 2 M pyridine solution and a basic fraction (sp-III) eluted with 2 M pyridine-acetic acid (pH 5.0).

The basic fraction sp-III was lyophilized, dissolved in 1.2 l of 0.5 N acetic acid, and adsorbed on a C$_{18}$ column ("LC-SORB sp-C-ODS", trade name; manufactured by Kemco Corporation). The column was eluted with an eluent [water:acetonitrile:10% trifluoroacetic acid (hereinafter called "TFA") =40:60:1], and the resultant eluate was lyophilized to obtain 5.1 g of sp-III as a dry product.

The dry product (5.1 g) of sp-III was dissolved in 1 N acetic acid. The thus-prepared solution was subjected in three portions to gel filtration on "Sephadex G-50" (column: 4.5×142 cm; flow rate: 40 ml/hour, fraction size: 50 ml/tube). Fraction Nos. 36-46 were lyophilized, dissolved in 1 N acetic acid and then subjected in two portions to gel filtration on "Sephadex G-25" (column: 4.5×140 cm; flow rate: 40 ml/hour; fraction size: 40 ml/tube). With respect to each of the resulting fractions, its relaxant activity for the chick rectum was investigated. Using the activity as an index, purification was proceeded with.

Figure 3:
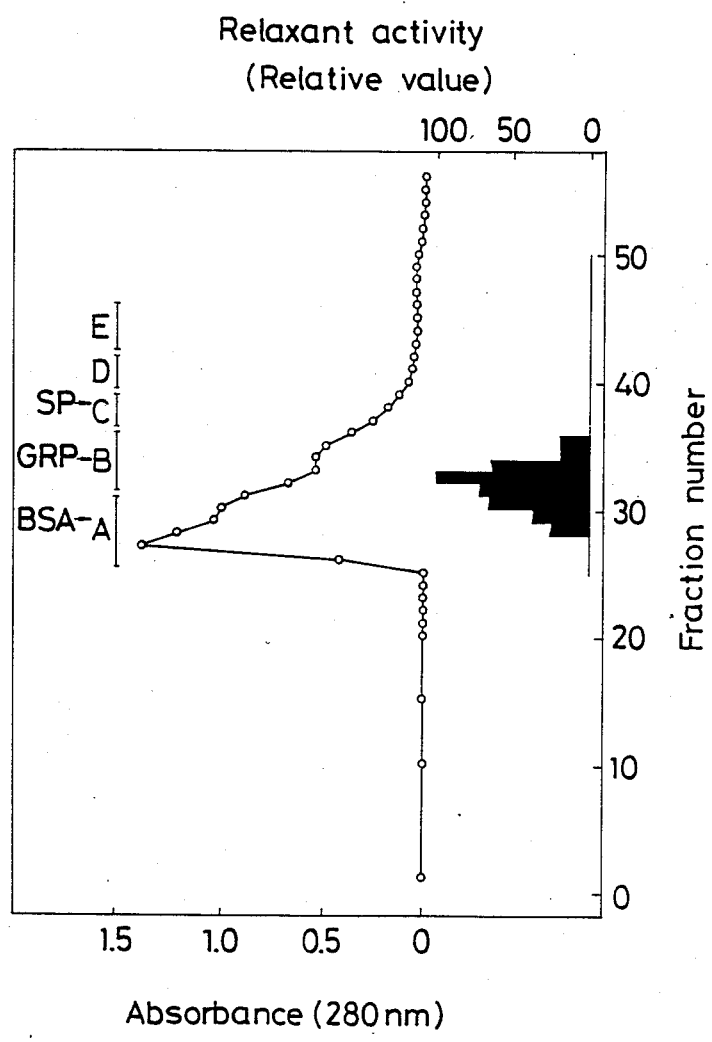
FIG. 3 depicts the relationship between the pattern of gel filtration of the basic fraction (sp-III) by "Sephadex G-25" in Example 1 and its relaxant activity for the chick rectum.

The relationship between the pattern of the gel filtration by "Sephadex G-25" and the relaxant activity for the chick rectum may be illustrated as shown in FIG. 3. Fractions A-E were obtained. Fraction B was lyophilized, and 410 mg of the resultant product was subjected to cation-exchange chromatography on "CM-52" (trade name; product of Wattman Corporation) under the following conditions: column: "CM-52" 2.4×45 cm; flow rate: 35 ml/hour; fraction size: 20 ml/tube; solvent system (A): 10 mM HCOONH$_4$ (pH 6.6):acetonitrile =90:10; solvent system (B): 0.5 M HCOONH$_4$ (pH 6.6): acetonitrile=90:10; eluted first with the solvent system (A) and then with the solvent system (B) in accordance with the linear gradient technique. Fraction Nos. 51-55, which showed relaxant activity for the chick rectum, were processed further by cation-exchange high-performance liquid chromatography in which the pH of each solvent was 3.8. Conditions [column: "TSK Gel CM-2SW" (trade name), 7.0×300 cm (manufactured by Toyo Soda Mfg. Co., Ltd.); flow rate: 3.0 ml/min; solvent system (A): 10 mM HCOONH$_4$ (pH 3.8):acetonitrile =90:10; solvent system (B): 1.0 M HCOONH$_4$ (pH 3.8): CH$_3$CN=90:10; eluted in accordance with the linear gradient technique while changing the ratio of (A):(B) from 100:0 to 50:50 in the course of 90 minutes]. Fractions having relaxant activity were obtained at retention time of 57–61.5 minutes.

The active fractions were purified by reversed-phase high-performance liquid chromatography. Conditions [column: "Kemco-sorb 7-diphenyl" (trade name), 4.6×250 mm (manufactured by Kemco Corporation); flow rate: 1.5 ml/min; solvent system (A): water:acetonitrile:10% TFA=90:10:1; solvent system (B): water: acetonitrile:10% TFA=40:60:1; eluted in accordance with the linear gradient technique while changing the ratio of (A):(B) from 100:0 to 0:100 in the course of 120 minutes]. In the above high-performance liquid chromatography, fractions having relaxant activity for the chick rectum were obtained at retention time of 43–46 minutes. These fractions were subjected further to reversed-phase high-performance liquid chromatography. Conditions [column: "Kemco-sorb 3-ODSH" (trade name), 8.0×75 mm (manufactured by Kemco Corporation); flow rate: 2.0 ml/min; solvent system (A): water: acetonitrile:10% TFA=90:10:1; solvent system (B): water:acetonitrile:10% TFA=40:60:1; eluted in accordance with the linear gradient technique while changing the ratio of (A):(B) from 80:20 to 0:100 in the course of 192 minutes]. By the above purification, active fractions were obtained at retention time of 27.8–29 minutes. The active fractions were purified further by reversed-phase high-performance liquid chromatography. Conditions [column: "Hitachi Gel #3063" (trade name), 1.2×150 mm (manufactured by Hitachi Ltd.); flow rate: 0.05 ml/min; solvent system (A): water:acetonitrile:10% TFA=100:0:1; solvent system (B): water:acetonitrile:10% TFA=40:60:1; eluted in accordance with the linear gradient technique while changing the ratio of (A):(B) from 70:30 to 45:55 in the course of 60 minutes]. Main peak at retention time of 45.2–46.4 minutes was collected, thereby obtaining about 1.5 μg of Peptide A in a substantially pure form.

EXAMPLE 2

Synthesis of Peptide A

In the synthesis of a protected peptide-resin conjugate, the α-amino group of each constituent amino acid was protected with a tert-butyloxycarbonyl group (Boc). In the active side chains, the hydroxyl group of Tyr was protected with a dichlorobenzyl group (Cl$_2$-Bzl), the guanidino group of Arg with a tosyl group (Tos), the β-carboxyl group of Asp with a benzyloxy group (OBzl), the hydroxyl group of Ser with a benzyl group (Bzl), and the thiol group of Cys with an acetamidomethyl group (Acm). The synthesis was conducted using 1.0 g of a chloromethyl resin with protected Tyr introduced therein.

Upon condensation of the protected amino acids, the chloromethyl resin was treated twice for 20 minutes each time at room temperature with trifluoroacetic acid (TFA), thereby removing almost completely the Boc group which was the protecting group for the terminal amino group of the protected Tyr coupled with the resin. The amino group which had been rendered free by the removal of the Boc group was condensed with the carboxyl group of the Boc-protected derivative of the amino acid located next in the amino acid sequence of the intended peptide. Where the protected amino acid was Boc-Arg (Tos) or Boc-Asn in the above condensation, the condensation was effected by treating 2 mmol of the Boc-amino acid with DCC in the presence of 1-hydroxybenztriazole. In the case of each remaining Boc-amino acid, the Boc-amino acid was treated with DCC to form a symmetric acid anhydride composed of two molecules of the Boc-amino acid, and 1 mmol of the symmetric acid anhydride was added. Where the reaction had not been brought to completion by the above procedure, the same procedure was repeated. The progress and completion of the reaction were monitored by the ninhydrin-dependent Kayser's test.

In the above-described manner, Boc-Asp(OBzl)-Ser(Bzl)-Gly-Cys(Acm)-Phe-Gly-Arg(Tos)-Arg(Tos)-Leu-Asp(OBzl)-Arg(Tos)-Ile-Gly-Ser(Bzl)-Leu-Ser(Bzl)-Gly-Leu-Gly-Cys(Tos)-Asn-Val-Leu-Arg(Tos)-Arg(Tos)-Tyr(Cl$_2$-Bzl)-resin [hereinafter called "Protected Peptide-Resin Conjugate (A)"]was synthesized from 1 g of the chloromethyl resin.

The deprotection and purification of Cys(Acm)-Peptide (A) were carried out in the following manner.

An HF reactor was charged with 700 mg of Protected Peptide-Resin Conjugate (A) and 1.5 ml of thioanisole, followed by introduction of 8 ml of HF. They were reacted at 0° C. for 40 minutes. Excess HF was thereafter distilled off. The residue was washed with 25 ml of ether to remove anisole, and the reaction product was then extracted with 20 ml of 1 N acetic acid. The resin and insoluble matter were removed by centrifugation. After diluting the extract tenfold in water, it was adsorbed on a column (2.0×40 cm) which was packed with 90 ml of an ODS resin ["LC-sorb", trade name; product of Kemco Corporation]. After washing the column thoroughly with 0.1 N acetic acid, the column was eluted with 200 ml of 60% acetonitrile which contained 0.1% of TFA. After driving off the acetonitrile under reduced pressure, the residue was lyophilized to obtain 301 mg of crude Cys(Acm)-Peptide (A). It was dissolved in 10 ml of 1 N AcOH. The resultant solution was subjected in 8 portions to reversed-phase high-performance liquid chromatography. Conditions [column: "Kemco-sorb 5, ODS-H" (trade name), 20×250 mm; flow rate: 5 ml/min; solvent system (A): water:acetonitrile:10% TFA=90:10:1; solvent (B): water:acetonitrile:10% TFA=40:60:1; eluted first at an (A):(B) ratio of 75:25 for 5 minutes, and then in accordance with the linear gradient technique while changing the ratio of (A):(B) to 25:75 in the course of 120 minutes]. That procedure was repeated 8 times to collect main peaks. After driving off the acetonitrile under reduced pressure, the residue was lyophilized to obtain 63.7 mg of Cys(Acm)-Peptide (A).

The removal of the Acm group from Cys(Acm)-Peptide(A) and the purification of the resultant product were conducted in the following manner. A solution (hereinafter called "Solution A") was provided by dissolving 227 mg of iodine in 50 ml of 95% acetic acid and then adding 80 μl of 1 N hydrochloric acid.

Another solution (hereinafter called "Solution B") was also provided by dissolving 2.1 g of citric acid and 575 mg of L-ascorbic acid and then adding water to 50 ml.

A solution of 63.7 mg of Cys(Acm)-Peptide(A) in 4 ml of 90% acetic acid was added dropwise at room temperature under stirring to 50 ml of Solution A, followed by stirring for further 20 minutes. Thereafter, Solution B was added dropwise until the brown color of iodine disappeared. The resultant mixture was added and diluted with 1,800 ml of water. It was adsorbed on a column (1.1×30 cm) which was packed with 29 ml of the ODS resin ("LC-sorb", trade name; product of Kemco Corporation). After washing the column thoroughly with 0.1 N acetic acid, the column was eluted with 60 ml of 60% acetonitrile which contained 0.1% of TFA. After driving off the acetonitrile under reduced pressure, the residue was lyophilized to obtain 57.0 mg of crude Peptide (A). It was dissolved in 3 ml of 10 mM ammonium formate which contained 10% of acetonitrile. The resultant solution was subjected in 3 portions to cation-exchange high-performance liquid chromatography. Conditions [column: "TSK Gel, CM-2SW" (trade name), 8×250 mm (manufactured by Toyo Soda Mfg. Co., Ltd.); flow rate: 2 ml/min; solvent system (A): 10 mM HCOONH$_4$ (pH 6.6):CH$_3$CN=90:10; solvent (B): 1 M HCOONH$_4$ (pH 6.6):CH$_3$CN=90:10; eluted first at an (A):(B) ratio of 85:15 for 1 minutes, and then in accordance with the linear gradient technique while changing the ratio of (A):(B) to 65:35 in the course of 140 minutes]. That procedure was repeated 3 times to collect a main peak eluted at 42–49 minutes. After driving off the acetonitrile under reduced pressure, the residue was adsorbed on a column (1.1×30 cm) which was packed with 29 ml of the ODS resin ["LC-sorb", trade name; product of Kemco Corporation]. After washing the column thoroughly with 0.1 N acetic acid, the column was eluted with 60 ml of 60% acetonitrile which contained 0.1% of TFA. After driving off the acetonitrile under reduced pressure, the residue was lyophilized to obtain 32.0 mg of Peptide (A).

EXAMPLE 3

Syntheses of H—Cys—Phe—Gly—Arg—Arg—Leu—Asp—Arg—
Ile—Gly—Ser—Leu—Ser—Gly—Leu—Gly—Cys—Asn—Val—Leu—Arg—Tyr—OH (Peptide B) and H—Asp—Ser—Gly—Cys—Phe—Gly—Arg—Arg—Leu—Asp—Arg—Ile—Gly—Ser—Leu—
Ser—Gly—Leu—Gly—Cys—Asn—Val—Leu—Arg—Tyr—OH (Peptide C)

After synthesizing Boc-Cys(Acm)-Phe-Gly-Arg(Tos)-Arg(Tos)-Leu-Asp(OBzl)-Arg(Tos)-Ile-Gly-Ser(Bzl)-Leu-Ser(Bzl)-Gly-Leu-Gly-Cys(Acm)-Asn-Val-Leu-Arg(Tos)-Tyr(Cl$_2$-Bzl)-resin [hereinafter called "Protected Peptide-Resin Conjugate (B)"] from 1.0 g of the chloromethyl resin in the same manner as in Example 2, a portion (220 mg) of Conjugate (B) was taken out. The remaining portion of Conjugate (B) was subjected further to an N-terminal extending reaction, thereby obtaining 1750 mg of Boc-Asp(OBzl)-Ser(Bzl)-Gly-Cys(Acm)-Phe-Gly-Arg(Tos)-Arg(Tos)-Leu-Asp(OBzl)-Arg(Tos)-Ile-Gly-Ser(Bzl)-Leu-Ser(Bzl)-Leu-Ser(Bzl)-Gly-Leu-Gly-Cys(Acm)-Asn-Val-Leu-Arg(Tos)-Tyr(Cl$_2$-Bzl)-resin [hereinafter called "Protected Peptide-Resin Conjugate (C)"].

The separation of Cys(Acm)-Peptide (B) from the resin an its purification were carried out in the following manner. The separation from the resin and the deprotection were conducted by treating 62 mg of Protected Peptide-Resin Conjugate (B) with HF in the same manner as in Example 2, thereby obtaining about 28 mg of crude Cys(Acm)-Peptide (B). It was then dissolved in 2 ml of 1 N AcOH, and the resultant solution was subjected to reversed-phase high-performance liquid chromatography. Conditions [column: "Kemco-sorb 5-ODS-H" (trade name), 20×250 mm (manufactured by Kemco Corporation); flow rate: 5 ml/min; solvent system (A): water:acetonitrile:10% TFA=90:10:1; solvent system (B): water:acetonitrile:10% TFA=40:60:1; 40:60:1; eluted first at an (A):(B) ratio of 75:25 for 5 minutes, and then in accordance with the linear gradient technique while changing the ratio of (A):(B) to 25:75 in the course of 120 minutes]. Main peaks were collected in the above procedure. After driving off the acetonitrile under reduced pressure, the residue was lyophilized to obtain 3.87 mg of Cys(Acm)-Peptide (B) in a substantially pure form. It was then subjected to Acm removal and cyclization with iodine in the same manner as in Example 2, thereby obtaining crude Peptide B. It was thereafter purified by reversed-phase high-performance liquid chromatography. Conditions [column: "Kemco-sorb 5-ODS-H" (trade name), 20×250 mm; flow rate: 5 ml/min; solvent system (A): water:acetonitrile:10% TFA=90:10:1; solvent system (B): water:acetonitrile:10% TFA=40:670:0.1; eluted first at an (A):(B) ratio of 75:25 for 5 minutes, and then in accordance with the linear gradient technique while changing the ratio of (A):(B) to 25:75 in the course of 120 minutes]. Main peaks eluted at 51.5–53 minutes respectively were collected. After driving off the acetonitrile under reduced pressure, the residue was lyophilized to obtain 1.97 mg of the intended Peptide B.

On the other hand, Peptide C was prepared in the following manner. The separation of Protected Peptide C from the resin and its deprotection were conducted by treating 565 mg of Protected Peptide-Resin Conjugate (C) with HF in the same manner as in Example 2. The resultant product was purified by reversed-phase high-performance liquid chromatography to obtain 29.3 mg of Cys(Acm)-Peptide (C).

A 5 mg portion of Cys(Acm)-Peptide (C) was then subjected to Acm removal and cyclization with iodine in the same manner as in Example 2, thereby obtaining 4.70 mg of crude Peptide C. It was thereafter dissolved in a 10 mM ammonium formate solution which contained 10% of acetonitrile. The resultant solution was subjected to ion-exchange high-performance liquid chromatography. Conditions [column: "TSK Gel CM-2SW" (trade name), 8.0×250 mm (manufactured by Toyo Soda Mfg. Co., Ltd.); flow rate: 2.0 ml/min; solvent system (A): 10 mM HCOONH4 (pH 6.6):acetonitrile=90:10; solvent system (B): 1 M HCOONH4 (pH 6.6):acetonitrile=90:10; eluted first at an (A):(B) ratio of 95:5 for 1 minute, and then in accordance with the linear gradient technique while changing the ratio of (A):(B) to 70:30 in the course of 140 minutes]. A main peak eluted at 58–64 minutes was collected. After driving off the acetonitrile under reduced pressure, the residue was adsorbed on "Seppack $C_{18}$ Cartridge" (trade name; manufactured by Millipore Corporation). After washing the cartridge with 3 ml of 0.1 N acetic acid, it was eluted with 5 ml of 60% acetonitrile which contained 0.1% of TFA. After driving off the acetonitrile under reduced pressure, the residue was lyophilized to obtain 1.87 mg of Peptide C.

EXAMPLE 4

Syntheses of H—Cys—Phe—Gly—Arg—Arg—Leu—Asp—Arg—Ile—Gly—Ser—Leu—Ser—Gly—Leu—Gly—Cys—Asn—Ser—Phe—Arg—Tyr—OH (Peptide D) and H—Asp—Ser—Gly—Cys—Phe—Gly—Arg—Arg—Leu—Asp—Arg—Ile—Gly—Ser—Leu—Ser—Gly—Leu—Gly—Cys—Asn—Ser—Phe—Arg—Tyr—OH (Peptide E)

After synthesizing Boc-Cys(Acm)-Phe-Gly-Arg(Tos)-Arg(Tos)-Leu-Asp(OBzl)-Arg(Tos)-Ile-Gly-Ser(Bzl)-Leu-Ser(Bzl)-Gly-Leu-Gly-Cys(Acm)-Asn-Ser(Bzl)-Phe-Arg(Tos)-Tyr($Cl_2$-Bzl)-resin [hereinafter called "Protected Peptide-Resin Conjugate (D)"]from 1 g of the chloromethyl resin in the same manner as in Example 2, a portion (275 mg) of Conjugate (D) was taken out. The remaining portion of Conjugate (D) was subjected further to an N-terminal extending reaction, thereby obtaining 587 mg of Boc-Asp(OBzl)-Ser(Bzl)-Gly-Cys(Acm)-Phe-Gly-Arg(Tos)-Arg(Tos)-Leu-Asp(OBzl)-Arg(Tos)-Ile-Gly-Ser(Bzl)-Leu-Ser(Bzl)-Gly-Leu-Gly-Cys(Acm)-Asn-Ser(Bzl)-Phe-Arg(Tos)-Tyr($Cl_2$-Bzl)-resin [hereinafter called "Protected Peptide-Resin Conjugate (E)"].

The separation of the Cys(Acm)-Peptide (D) from the resin and its purification were carried out in the following manner. The separation from the resin and the deprotection were conducted by treating 128 mg of Protected Peptide-Resin Conjugate (D) with HF in the same manner as in Example 2 and then purifying the resultant product in accordance with reversed-phase high-performance liquid chromatography, thereby obtaining 16.8 mg of Cys(Acm)-Peptide (D). Using 7.13 mg of Cys(Acm)-Peptide (D), the removal of Acm and cyclization were performed with iodine in the same manner as in Example 2 so that crude Peptide D was obtained. Crude Peptide D was then purified by reversed-phase high-performance liquid chromatography. Conditions [column: "Kemco-sorb 5-ODS-H" (trade name), 20×250 mm; flow rate: 5 ml/min; solvent system (A): water:acetonitrile:10% TFA=90:10:1; solvent system (B): water:acetonitrile:10% TFA=40:60:1; eluted first at an (A):(B) ratio of 75:25 for 5 minutes, and then in accordance with the linear gradient technique while changing the ratio of (A):(B) to 25:75 in the course of 120 minutes]. A main peak eluted at 46-52 minutes was collected. After driving off the acetonitrile under reduced pressure, the residue was lyophilized to obtain 4.03 mg of Peptide D.

On the other hand, Peptide E was prepared in the following manner. The separation of Protected Peptide E from the resin and its deprotection were conducted by treating 300 mg of Protected Peptide-Resin Conjugate (E) with HF in the same manner as in Example 2. The resultant product was purified by reversed-phase high-performance liquid chromatography to obtain 38.0 mg of Cys(Acm)-Peptide (E). It was then subjected to Acm removal and cyclization with iodine in the same manner as in Example 2, thereby obtaining 36.7 mg of crude Peptide E. It was thereafter purified by ion-exchange high-performance liquid chromatography. Conditions [column: "TSK Gel CM-2SW" (trade name), 8.0×250 mm (manufactured by Toyo Soda Mfg. Co., Ltd.); flow rate: 2.0 ml/min; solvent system (A): 10 mM $HCOONH_4$ (pH 6.6):$CH_3CN$=90:10; solvent system (B): 1 M $HCOONH_4$ (pH 6.6):$CH_3CN$=90:10; eluted first at an (A):(B) ratio of 100:0 for 1 minute, and then in accordance with the linear gradient technique while changing the ratio of (A):(B) to 70:30 in the course of 140 minutes]. A main peak eluted at 64-70 minutes was collected. After driving off the acetonitrile under reduced pressure, the residue was adsorbed on a column (1.1×30 cm) which was packed with 29 ml of the ODS resin ["LC-sorb"(trade name), product of Kemco Corporation]. After washing the column thoroughly with 0.1 N acetic acid, it was eluted with 60 ml of 60% acetonitrile which contained 0.1% of TFA. After driving off the acetonitrile under reduced pressure, the residue was lyophilized to obtain 22.7 mg of Peptide E.

EXAMPLE 5

Synthesis of H—Asp—Ser—Gly—Cys—Phe—Gly—Arg—Arg—Leu—Asp—Arg—Ile—Gly—Ser—Leu—Ser—Gly—Leu—Gly—Cys—Asn—Val—Leu—Arg—Arg—OH (Peptide F)

A solution (hereinafter called "Solution E") was provided by adding 200 μl of 50 mM tris-HCl buffer (pH 8.0) to 4 μl of a 10% LiCl solution (enzyme concentration: 1 mg/ml) of carboxypeptidase A (product of Sigma Chemical Company). Peptide A (10 μg) was dissolved in 40 μl of 50 mM tris-HCl buffer (pH 8), followed by an addition of 10 μl of Solution E. After allowing the resultant mixture to stand at 37° C. for 1 hour, 50 μl of 2% TFA was added. The thus-prepared mixture was subjected directly to reversed-phase high-performance liquid chromatography. Conditions [column: "TSK LS ODS SIL" (trade name), 4.0×250 mm; flow rate: 2 ml/min; solvent system (A): water:acetonitrile:10% TFA=90:10:1; solvent system (B): water:acetonitrile:10% TFA=40:60:0.1; eluted first at an (A):(B) ratio of 100:0 for 4 minutes, and then in accordance with the linear gradient technique while changing the ratio of (A):(B) to 0:100 in the course of 40 minutes]. A main peak eluted at 21.5 minutes was collected. After driving off the acetonitrile under reduced pressure, the residue was lyophilized to obtain 4.3 μg of Peptide E.

EXAMPLE 6

Synthesis of H—Asp—Ser—Gly—Cys—Phe—Gly—Arg—Arg—
                              |
Leu—Asp—Arg—Ile—Gly—Ser—Leu—Ser—Gly—Leu—Gly—Cys—Asn—Val—Leu—Arg—OH (Peptide G)

Following the procedure of Example 4, 100 μg of Peptide C was treated with carboxypeptidase A (product of Sigma Chemical Company) and then purified by reversed-phase high-performance liquid chromatography. Conditions [column: "Nucleosil 120-C18" (trade name), 4.6×75 mm, manufactured by Kemco Corporation; flow rate: 1 ml/min; solvent system (A): water:acetonitrile:10% TFA=90:10:1; solvent system (B): water:acetonitrile:10% TFA=40:60:1; eluted first at an (A):(B) ratio of 100:0 for 4 minutes, and then in accordance with the linear gradient technique while changing the ratio of (A):(B) to 0:100]. A main peak eluted at 24.4 minutes was collected. After driving off the acetonitrile under reduced pressure, the residue was lyophilized to obtain 75 μg of Peptide G.

EXAMPLE 7

Synthesis of H—Asp—Ser—Gly—Cys—Phe—Gly—Arg—Arg—
                              |
Leu—Asp—Arg—Ile—Gly—Ser—Leu—Ser—Gly—Leu—Gly—Cys—Asn—Val—Leu—OH (Peptide H)

A solution of carboxypeptidase B (product of Sigma Chemical Company) in 50 mM tris-HCl buffer (pH 8.0) (enzyme concentration: 10 μg/ml; hereinafter called "Solution F") was provided. Peptide F (3.5 μg was added with 160 μl of 50 mM tris-HCl buffer (pH 8.0) and 20 μl of 0.1% Triton X-100, thereby dissolving Peptide F. Solution F (20 μl) was added to the resultant solution, and the thus-prepared mixture was left over at 37° C. for 10 minutes. Thereafter, 200 μl of 2% TFA was added, followed by reversed-phase high-performance liquid chromatography. Conditions [column: "TSK LS ODS SIL" (trade name), 4.0×250 mm; flow rate: 2 ml/min; solvent system (A): water:acetonitrile:10% TFA=90:10:1; solvent system (B): water:acetonitrile:10% TFA=40:60:1; eluted first at an (A):(B) ratio of 100:0 for 4 minutes, and then in accordance with the linear gradient technique while changing the ratio of (A):(B) to 0:100 in the course of 40 minutes]. A main peak eluted at 24.0 minutes was collected. After driving off the acetonitrile under reduced pressure, the residue was lyophilized to obtain 3.0 μg of Peptide H.

Physical and chemical properties of Peptides A–H obtained above in Examples 1–7 respectively were as follows.

(1) Appearance:
 White powder.
(2) Solubility in solvents:
 Soluble in water, aqueous acidic solutions and acetic acid. Insoluble in chloroform, benzene, ethyl ether and hexane.
(3) Distinction of acidic, neutral or basic:
 Basic.
(4) Amino acid compositions:
 See Table 2.

TABLE 2

| Peptide | A | B | C | D | E | F | G | H |
|---|---|---|---|---|---|---|---|---|
| Molecular weight | 2869.33 | 2454.90 | 2713.15 | 2475.87 | 2735.09 | 2706.16 | 2549.98 | 2393.79 |
| Amino acid composition* | Found (Calc'd) | Found (Calc'd) | Found (Calc'd) | Found (Calc'd) | Found (Calc'd) | Found (Calc'd) | Found (Calc'd) | Found (Calc'd) |
| Asp + Asn | 3.00(3) | 1.99(2) | 3.02(3) | 2.08(2) | 3.10(3) | 3.12(3) | 3.01(3) | 3.12(3) |
| Ser | 2.56(3) | 1.77(2) | 2.68(3) | 2.73(3) | 3.60(4) | 2.72(3) | 2.70(3) | 2.75(3) |
| Gly | 4.88(5) | 3.94(4) | 4.95(5) | 4.03(4) | 5.03(5) | 4.95(5) | 4.94(5) | 5.01(5) |
| Cys** | 1.62(2) | 1.61(2) | 1.62(2) | 1.67(2) | 1.67(2) | 1.62(2) | 1.65(2) | 1.59(2) |
| Val | 1.00(1) | 1.00(1) | 1.00(1) |  |  | 1.00(1) | 1.00(1) | 1.00(1) |
| Ile | 0.95(1) | 0.96(1) | 0.96(1) | 0.97(1) | 0.97(1) | 0.95(1) | 0.97(1) | 0.96(1) |
| Leu | 4.06(4) | 4.06(4) | 4.09(4) | 3.07(3) | 3.05(3) | 4.00(4) | 4.06(4) | 4.05(4) |
| Tyr | 1.08(1) | 1.14(1) | 1.15(1) | 1.13(1) | 1.14(1) |  |  |  |
| Phe | 0.98(1) | 0.99(1) | 1.00(1) | 2.00(2) | 2.00(2) | 1.08(1) | 1.02(1) | 1.03(1) |
| Arg | 5.02(5) | 3.98(4) | 3.99(4) | 4.03(4) | 4.02(4) | 4.97(5) | 3.98(4) | 3.02(3) |

*The found values in the table were obtained as a result of amino acid analyses and are expressed in terms of molar ratio.
**Measured by oxidizing with performic acid, hydrolyzing and recovering as Cys—SO₃H. The order amino acids were measured by hydrolyzing with 6 N HCl.

We claim:
1. A substantially pure physiologically-active peptide represented by the formula (I):

X—Cys—Phe—Gly—Arg—Arg—Leu—Asp—Arg—Ile    (I)
    |                                                                    
    —Gly—Ser—Leu—Ser—Gly—Leu—Gly—Cys—Y wherein X means H or H-Asp-Ser.-Gly- and Y denotes -Asn-Val-Leu-Arg-Arg-Tyr-OH, -Asn-Val-Leu-Arg-OH, -Asn-Val-Leu-Arg-Tyr-OH, -Asn-Val-Leu-Arg-OH, -Asn-Val-Leu-OH or Asn-Ser-Phe-Arg-Tyr-OH, or a salt thereof.

2. The peptide of claim 1, wherein X is H.
3. The peptide of claim 1, wherein X is H-Asp-Ser-Gly-.
4. The peptide of claim 1, wherein Y is -Asn-Val-Leu-Arg-Arg-Tyr-OH.
5. The peptide of claim 1, wherein Y is -Asn-Val-Leu-Arg-Arg-OH.
6. The peptide of claim 1, wherein Y is -Asn-Val-Leu-Arg-Tyr-OH.

7. The peptide of claim 1, wherein Y is -Asn-Val-Leu-Arg-OH.

8. The peptide of claim 1, wherein Y is -Asn-Val-Leu-OH.

9. The peptide of claim 1, wherein Y is -Asn-Ser-Phe-Arg-Tyr-OH.

10. The peptide of claim 1, wherein said salt is selected from the group consisting of hydrochloric acid, sulfuric acid, phosphoric acid, formic acid, acetic acid, citric acid, tartaric acid, fumaric acid and maleic acid salts.

* * * * *